United States Patent [19]

Kaneko et al.

[11] Patent Number: 4,660,567

[45] Date of Patent: Apr. 28, 1987

[54] METHOD OF AUTOMATICALLY MEASURING BLOOD PRESSURE, AND APPARATUS THEREFOR

[75] Inventors: Yoshihiro Kaneko; Osamu Tochikubo, both of Yokohama; Hiroyuki Yokoi, Sakado, all of Japan

[73] Assignee: Takeda Medical Company Limited, Tokyo, Japan

[21] Appl. No.: 726,764

[22] Filed: Apr. 24, 1985

[30] Foreign Application Priority Data

Sep. 27, 1984 [JP] Japan .................................. 59-200503
Sep. 27, 1984 [JP] Japan .................................. 59-200504
Sep. 27, 1984 [JP] Japan .................................. 59-200505

[51] Int. Cl.$^4$ ............................................. A61B 5/02
[52] U.S. Cl. ................................... 128/682; 128/680
[58] Field of Search ...................... 126/672, 677-686

[56] References Cited

U.S. PATENT DOCUMENTS

| | | | |
|---|---|---|---|
| 3,550,582 | 12/1970 | Wilhelmson | 128/683 |
| 3,636,941 | 1/1972 | Guevrekian | 128/683 |
| 3,744,490 | 7/1973 | Fernandez | 128/683 |
| 3,814,083 | 6/1974 | Fletcher et al. | 128/683 |
| 4,214,589 | 7/1980 | Sakamoto et al. | 128/680 |
| 4,326,536 | 4/1982 | Kitagawa et al. | 128/682 |
| 4,343,314 | 8/1982 | Sramek | 128/680 |
| 4,549,549 | 10/1985 | Furukawa | 128/680 |

FOREIGN PATENT DOCUMENTS

1460413 1/1977 United Kingdom .
2087238A 5/1982 United Kingdom .

OTHER PUBLICATIONS

"Automatic Non-Invasive Blood Pressure and Heat Rate Monitoring with Tabular and Trend Write-Outs'—Del Mar Avionics (1978).

"Blood Pressure by Oscillometry", Joseph Looney, Jr., Applied Medical Research—Medical Electronics, Apr. 1978.

"Comparision of Indirect Pressure Measurements (Korotkoff) with Simultaneous Direct Brachial Artery Pressure Distal to the Cuff", Seymour B. London and Rose E. London—Advances in Internal Medicine, vol. 13, pp. 127-142.

*Primary Examiner*—Kyle L. Howell
*Assistant Examiner*—Angela D. Sykes
*Attorney, Agent, or Firm*—Staas & Halsey

[57] ABSTRACT

Method and apparatus are disclosed for linearly pressurizing a cuff, affixed to the limb of a patient, with gas from a liquified gas tank, monitoring Korotkoff sounds that appear and disappear during cuff pressurization to ascertain approximate systolic and diastolic blood pressures as cuff pressurization is in process, halting pressurization at a point slightly higher than the approximate systolic blood pressure and then immediately depressurizing the cuff at a regulated rate to actually measure and determine true systolic blood pressure. Following the determination of systolic blood pressure, the cuff is depressurized at a rapid rate down to a point slightly higher than the approximate diastolic blood pressure and is then depressurized again at the regulated rate again to actually measure and determine true diastolic blood pressure. When a Korotkoff sound cannot be found during attempted actual measurement of the diastolic blood pressure, the currently prevailing cuff pressure is raised by a predetermined amount and the cuff is then vented again at the regulated rate to remeasure and redetermine diastolic blood pressure for the purpose of covering any fluctuation in the patient's blood pressure.

10 Claims, 18 Drawing Figures

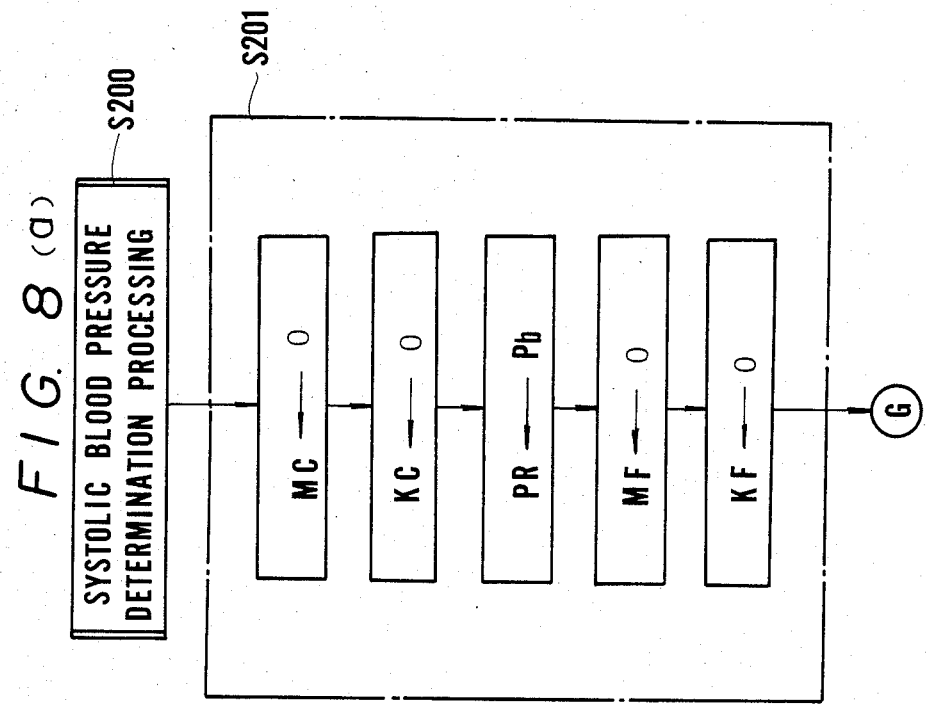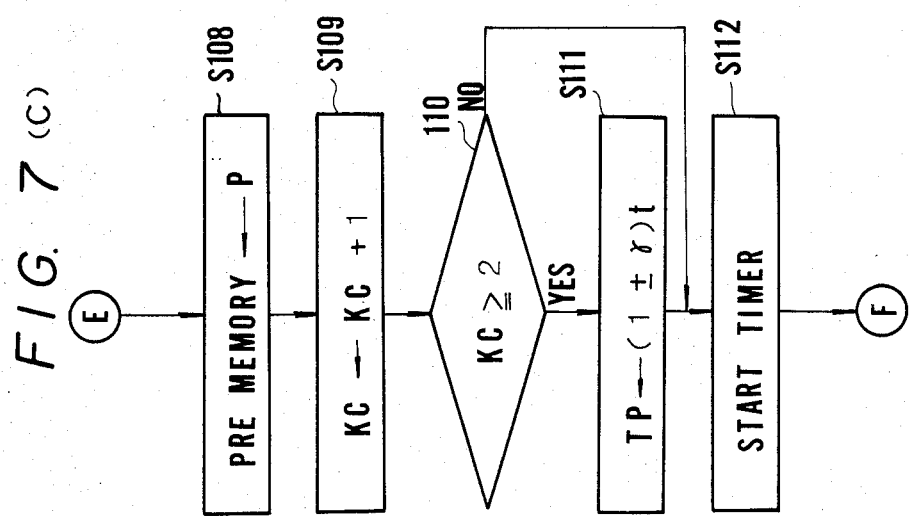

METHOD OF AUTOMATICALLY MEASURING BLOOD PRESSURE, AND APPARATUS THEREFOR

BACKGROUND OF THE INVENTION

1. Field of the Invention

This invention relates to a method and apparatus for automatically measuring blood pressure by a noninvasive method. More particularly, the present invention relates to an automatic blood pressure measurement method and apparatus for shortening a measurement process which includes automatically halting cuff pressurization near the systolic blood pressure of a patient, allowing cuff pressure to diminish, determining the systolic blood pressure and then measuring the diastolic blood pressure

2. Description of the Prior Art

In the conventional automatic sphygmomanometer which operates on the basis of the indirect ausculcation method, the pressure applied to a cuff affixed to a limb of a patient is controlled by presetting a pressurization cut-off point (e.g., 150–200 mmHg) high enough to cover the systolic blood pressure of a typical patient, and pressurizing the cuff until this preset value is attained. Accordingly, if we assume that the rate at which pressure is released from the cuff is constant, the time needed to measure blood pressure is prolonged by an amount corresponding to pressurization of the cuff over and above the systolic blood pressure of the patient. Moreover, for a constant pressure-release rate of 2–3 mmHg/sec, several heartbeats in the vicinity of the systolic blood pressure are all that are required when determining such blood pressure. Pressurizing the cuff beyond what is needed to detect these heartbeats requires time that is unnecessary for measurement for all practical purposes. This not only causes the patient discomfort but is also detrimental to achieving rapid measurement for ascertaining a short-term fluctuation in blood pressure.

The blood pressure measurement process with the conventional automatic sphygmomanometer of the above-described type comprises initially pressurizing the cuff to the set value (e.g., 150–200 mmHg) and then depressurizing the cuff at a constant rate (e.g., 2–3 mmHg/sec) of pressure release. Thus, determination of the systolic and diastolic blood pressures is performed by a continuous measurement spanning the interval between these two points. The time required for blood pressure measurement is therefore dependent upon the blood pressure value (pulse pressure) of the patient, assuming that the cuff venting rate is constant. Since the flow of blood during the aforementioned interval is almost completely cut off by occlusion, a state of blood congestion continues for the duration and often results in an erroneous determination of diastolic blood pressure. Furthermore, to perform a meaningful measurement, only a few heartbeats in the vicinity of the systolic and diastolic blood pressures are needed. Measurement conducted at a regulated venting rate during other intervals requires time which is wasted for practical purposes. And as mentioned above, the longer the time needed for measurement, the greater the discomfort experienced by the patient and the more difficult it is to realize high-speed measurement for ascertaining rapid fluctuations in blood pressure.

The aforementioned automatic sphygmomanometer according to the prior art employs a diaphragm-type pump or piston-type pump as the cuff pressurizing means. Noise emitted by the pressurizing means whenever a measurement is taken is a cause of stress not only for the patient but for those in the vicinity. Moreover, since a patient undergoing long-term monitoring of his or her blood pressure will tend to be awakened at night by the noise from the pressurizing means, it is difficult to ascertain the dynamics of the patient's blood pressure during sleep.

SUMMARY OF THE INVENTION

An object of the present invention is to provide an automatic blood pressure measuring apparatus capable of measuring blood pressure in a shorter period of time by automatically halting cuff pressurization in the vicinity of a patient's systolic blood pressure and then allowing cuff pressure to decline.

Another object of the present invention is to provide an automatic blood pressure measuring apparatus completely free of pressurizing noise caused by a pump or the like.

Still another object of the present invention is to provide an automatic blood pressure measuring apparatus which is compact, light in weight and capable of long periods of continuous service.

A further object of the present invention is to provide an automatic blood pressure measuring method and apparatus whereby blood pressure can be measured quickly and accurately by curtailing the measurement process through which cuff pressure is reduced to a point near diastolic blood pressure at a constant rate following determination of systolic blood pressure.

A yet further object of the present invention is to provide an automatic blood pressure measuring method and apparatus whereby blood pressure can be measured quickly and accurately by curtailing the measurement process through which cuff pressure is reduced to a point near diastolic blood pressure at a constant rate following determination of systolic blood pressure, and by taking into account the fact that measurement of diastolic blood pressure may be rendered impossible by a fluctuation in the blood pressure of the patient.

According to the present invention, the foregoing objects are attained by providing an apparatus for automatically measuring blood pressure, comprising pressurizing means for elevating the pressure of a cuff affixed to a limb of a patient, K-sound sensing means for sensing K-sounds from the patient and for producing a K-sound signal indicative of the sensed K-sounds, setting means for monitoring the K-sound signal produced by the K-sound sensing means following actuation of the pressurizing means and for setting a pressurization cut-off point, and control means for deactuating the pressurizing means when the K-sound signal fails to be sensed by the time the set pressurization cut-off point is attained.

According to a modification of the present invention, the setting means includes means for obtaining a K-sound signal generation period on the basis of a plurality of previous K-sounds, and for obtaining in accordance with said period a time lapse from an immediately preceding K-sound, the moment of the time lapse serving as the pressurization cut-off point. If only one K-sound signal is detected during the course of pressurization, the setting means obtains a prescribed time lapse from this point, the moment of the time lapse serving as the pressurization cut-off point.

According to another modification of the present invention, the pressurizing means comprises a liquified gas tank as a source of pressure.

According to the present invention, the foregoing objects are attained by providing a method of automatically measuring blood pressure, comprising steps of monitoring a K-sound signal during pressurization of a cuff affixed to a limb of a patient and setting a rapid-rate depressurization cut-off point, determining systolic blood pressure based on a K-sound signal sensed during constant-rate depressurization of the cuff following termination of pressurization, and rapidly depressurizing the cuff down to the rapid-rate depressurization cut-off point following determination of the systolic blood pressure.

According to another aspect of the present invention, the foregoing objects are attained by providing an apparatus for automatically measuring blood pressure, comprising pressurizing means for elevating the pressure of a cuff affixed to a limb of a patient, first depressurizing means for reducing the pressure of the cuff at a predetermined rate, second depressurizing means for reducing the pressure of the cuff at a rate higher than the predetermined rate, pressure sensing means for sensing the pressure of the cuff, K-sound sensing means for sensing K-sounds from the patient and for producing a K-sound signal indicative of the sensed K-sounds, setting means for monitoring the K-sound signal while the pressurizing means is operational and for setting a rapid-rate depressurization cut-off point, systolic blood pressure determining means for determining systolic blood pressure based on a K-sound signal sensed while the first depressurizing means is operational following termination of pressurization, and depressurization control means for actuating the second depressurizing means in response to determination of the systolic blood pressure thereby to reduce the pressure of the cuff down to the rapid-rate depressurization cut-off point.

According to a modification of the present invention, the setting means includes means for adding a first predetermined pressure value to a diastolic blood pressure when the diastolic blood pressure is capable of being predicted based on the K-sound signal, the resulting diastolic blood pressure value serving as the rapid-rate depressurization cut-off point.

According to another modification of the present invention, the setting means includes means for subtracting, when diastolic blood pressure cannot be predicted by monitoring the K-sound signal, a second predetermined pressure value from the cuff pressure which prevails when the systolic blood pressure is determined, the resulting pressure value serving as the rapid-rate depressurization cut-off point.

The pressurizing means comprises a liquified gas tank as a source of pressure.

According to this other aspect of the present invention, the foregoing objects are attained by providing a method of automatically measuring blood pressure, comprising steps of monitoring a K-sound signal during pressurization of a cuff affixed to a limb of a patient and setting a rapid-rate depressurization cut-off point, determining systolic blood pressure based on a K-sound signal sensed during constant-rate depressurization of the cuff following termination of pressurization, rapidly depressurizing the cuff down to the rapid-rate depressurization cut-off point following determination of the systolic blood pressure, determining diastolic blood pressure based on a K-sound signal sensed during constant-rate depressurization of the cuff following termination of rapid-rate depressurization, and performing a redetermination of diastolic blood pressure by first elevating the pressure of the cuff a predetermined amount upon discriminating that a K-sound signal fails to be sensed in a predetermined interval of time during constant-rate depressurization of the cuff following termination of rapid-rate depressurization, and then determining diastolic blood pressure based on a K-sound signal sensed during constant-rate depressurization of the cuff following termination of the elevation in pressure.

According to still another aspect of the present invention, the foregoing objects are attained by providing an apparatus for automatically measuring blood pressure, comprising pressurizing means for elevating the pressure of a cuff affixed to a limb of a patient, first depressurizing means for reducing the pressure of the cuff at a predetermined rate, second depressurizing means for reducing the pressure of the cuff at a rate higher than the predetermined rate, pressure sensing means for sensing the pressure of the cuff, K-sound sensing means for sensing K-sounds from the patient and for producing a K-sound signal indicative of the sensed K-sounds, setting means for monitoring the K-sound signal while the pressurizing means is operational and for setting a rapid-rate depressurization cut-off point, systolic blood pressure determining means for determining systolic blood pressure based on a K-sound signal sensed while the first depressurizing means is operational following termination of pressurization, depressurization control means for actuating the second depressurizing means in response to determination of the systolic blood pressure thereby to reduce the pressure of the cuff down to the rapid-rate depressurization cut-off point, diastolic blood pressure determining means for determining diastolic blood pressure based on a K-sound signal sensed while the first depressurizing means is operational following termination of depressurization, and redetermination means for elevating the pressure of the cuff a predetermined amount upon discriminating that a K-sound signal fails to be sensed in a predetermined interval of time during operation of the first depressurizing means following termination of depressurization, and for determining diastolic blood pressure based on a K-sound signal sensed during operation of the first depressurizing means following termination of the elevation in pressure.

According to a modification of the present invention, the setting means includes means for adding a first predetermined pressure value to a diastolic blood pressure when the diastolic blood pressure is capable of being predicted based on the K-sound signal, the resulting diastolic blood pressure value serving as the rapid-rate depressurization cut-off point.

According to another modification of the present invention, the setting means includes means for subtracting, when diastolic blood pressure cannot be predicted by monitoring the K-sound signal, a second predetermined pressure value from the cuff pressure which prevails when the systolic blood pressure is determined, the resulting pressure value serving as the rapid-rate depressurization cut-off point.

The pressurizing means comprises a liquified gas tank as a source of pressure.

According to the present invention, cuff pressurization is cut off automatically at the minimum pressure necessary for measuring a patient's systolic blood pressure. As a result, soon after the start of constant-rate venting of pressure from the cuff, several heartbeats appear in the vicinity of the systolic blood pressure to make possible highly efficient measurement of blood pressure in a short period of time. Furthermore, sources of pulsation and noise such as diaphragm- or piston-type pumps are not employed as the source of pressure for inflating the cuff, thereby allowing cuff pressure to be elevated without pulsation, i.e., in linear fashion, so that the appearance and disappearance of Korotkoff sounds at pressurization can be accurately detected. Moreover, since there is no source of noise, patients in the vicinity are not subjected to stress and a patient that requires constant, long-term monitoring of blood pressure will not be awakened even when measurements are taken continuously at night. This permits the dynamics of a patient's blood pressure during sleep to be ascertained correctly.

Since the source for pressurization of the cuff employs a liquified gas tank, the apparatus can be reduced in size and weight and the tank is capable of inflating the cuff many times despite its small capacity. Accordingly, the pressure source has a long service life even if the apparatus is carried about and used frequently.

Further, according to the invention, it is possible to curtail a process for constant-rate pressure release down to the vicinity of a patient's diastolic blood pressure once systolic blood pressure has been determined. This feature enables blood pressure to be measured in rapid and yet accurate fashion and makes it possible to perform a high-speed blood pressure measurement for ascertaining short-term fluctuations in blood pressure not heretofore feasible with the prior art. Since the liquified gas tank raises cuff pressure linearly without pulsation, as mentioned above, the appearance and disappearance of Korotkoff sounds during pressurization are accurately detected. This serves as a basis for accurately predicting diastolic blood pressure so that the curtailment of the constant-rate depressurization process can be performed without jeopardizing reliability. Furthermore, even if the patient's blood pressure should happen to fluctuate during such curtailment of constant-rate depressurization down to the vicinity of diastolic blood pressure following determination of systolic blood pressure, a highly efficient retrial measurement is performed whereby cuff pressure is controlled automatically so as to fully cover the patient's diastolic blood pressure. Therefore, reliable, high-speed measurement of blood pressure is conducted essentially by a single measurement cycle. Here the liquified gas tank, besides elevating cuff pressure in linear fashion, also facilitates the control of cuff pressurization and depressurization. This enables the retrial process to be executed in a positive and rapid manner.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 7(a), 7(b), and 7(c) are a flowchart illustrating an optimum pressurization control processing sequence performed by pressure control means included in the apparatus of FIG. 1;

DESCRIPTION OF THE PREFERRED EMBODIMENT

Figure 1:
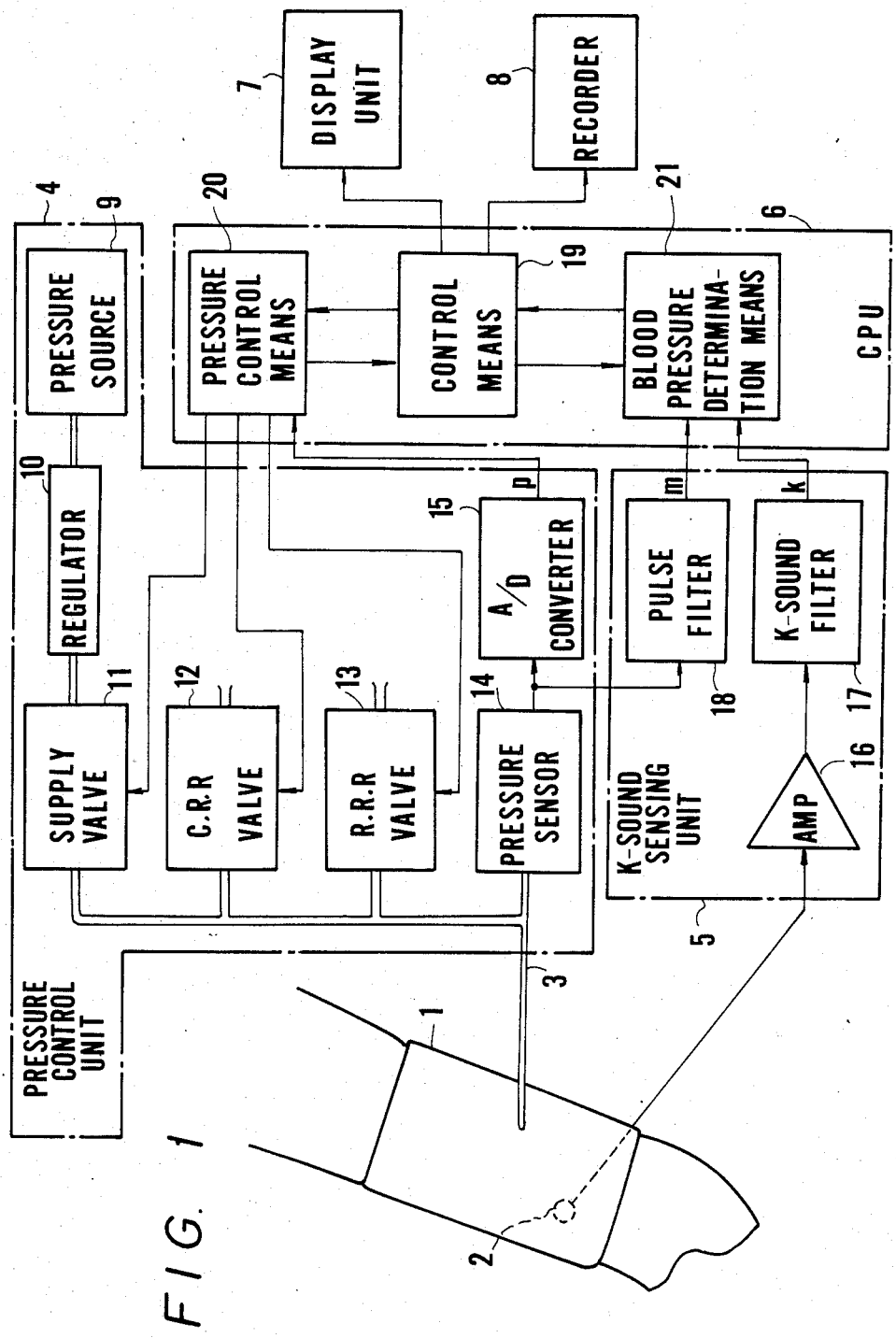
FIG. 1 is a block diagram illustrating an embodiment of an automatic blood pressure measuring apparatus according to the present invention.

There is shown in FIG. 1 a block diagram of an apparatus for automatically measuring blood pressure according to a preferred embodiment of the present invention. A cuff 1 wrapped about the arm of a patient contains a microphone 2 for sensing Korotkoff sounds, referred to hereinafter as K-sounds. The cuff 1 is connected to the main part of the apparatus by a pipe 3 in order that the cuff pressure may be detected and controlled. The main part of the apparatus is basically composed of three principal units, namely a pressure control unit 4 for detecting and controlling cuff pressure via the pipe 3, a K-sound sensing unit 5 connected to the microphone 2 for sensing K-sounds, and a central processing unit (CPU) 6 which has overall control of the apparatus. The CPU 6 is connected to a display unit 7, with which the apparatus is ordinarily equipped, for displaying such information as the systolic and diastolic blood pressures of the patient, and to a recorder for recording the information, the latter connection being made when it is desired to measure blood pressure automatically over an extended period of time.

The pressure control unit 4 comprises a pressure source 9 constituted by a tank filled with liquified oxygen or liquified carbon dioxide gas ($CO_2$), or a tank filled with compressed air or the like, a regulator 10 for regulating the pressure of the gas, which is delivered by the pressure source 9, to a constant value, a supply valve 11 for pressurizing the cuff 1 with the gas from the regulator 10, a constant-rate release valve 12 for venting the cuff pressure at a constant rate (e.g., 2–3 mmHg/sec), a rapid-rate release valve 13 for dumping cuff pressure at a rapid rate, a pressure sensor 14 for sensing the cuff pressure and for converting the sensed pressure into an analog electric signal, and an A/D converter 15 for converting the analog signal output of the pressure sensor 14 into a digital signal p. According to the illustrated embodiment of the present invention, the pressure source 9 does not employ a pump, thereby completely eliminating noise ordinarily associated with pressurization of the cuff 2. The reason for replacing the pump with a gas tank is to readily obtain a non-pulsating, rising characteristic when the cuff pressure is being raised. The advantage of elevating cuff pressure in linear fashion will become clear from the description to follow. It is preferred that a liquified gas tank be used, for this will render the pressure source 9 small in size and light in weight. Such a tank permits many inflations of the cuff despite its small capacity. By way of example, a liquified $CO_2$ tank having a diameter of 30 mm and a length of 120 mm is capable of being used continually for 100 measurement operations and can be carried at, say, the patient's waist in such a manner as not to apply a load to the patient.

The K-sound sensing unit 5 comprises an amplifier 16 for preamplifying the weak K-sound signal detected by the microphone 2, a K-sound filter 17 for sampling predetermined frequency components extracted from the output signal of the amplifier 16 and for comparing the amplitudes thereof to isolate signals corresponding to the K-sounds, and for shaping an isolated signal into a pulse delivered as a K-sound signal k, and a patient pulse filter 18 for isolating an amplitude signal component contained in the output signal of the pressure sensor 14 and representative of the amplitude of oscillation of the patient's pulse pressure, and for shaping the isolated component into a pulse delivered as a signal m synchronized to the pulse of the patient. The signal m is for the purpose of picking up throbbing motion of the patient's blood vessel, which has been occluded by the cuff 1, when the pressure applied to the cuff 1 is gradually diminished. It is known that the signal m generally manifests itself before and vanishes after the K-sounds. Accordingly, a very weak K-sound is accurately detected among so-called artifact noise by thus extracting the amplitude signal component through the filter 18 and using this component as a gate signal for K-sound detection.

Though the hardware constituting the CPU6 is not shown in detail, the CPU includes a ROM (read-only memory) storing a processing program as embodied in FIGS. 6 through 9, a microprocessor for executing the program, a RAM (random-access memory) required for data processing, a PIO (parallel input-output interface) for input and output of processed data, and a driver circuit for driving the valves 11 through 13. The CPU block 6 is shown to be composed of blocks indicating various functions implemented by execution of the processing program. These function blocks are control means 19 for overall control of the CPU 6, pressure control means 20 which, under the control of control means 19, reads the cuff pressure detection signal p produced by the A/D converter 15 and controls the valves 11 through 13 so as to achieve prescribed pressurized and depressurized states internally of the cuff 1, and blood pressure determining means 21 which, under the control of the control means 19, determines the patient's systolic and diastolic blood pressures by examining the K-sound signal k which appears during the signal m.

Figure 2:
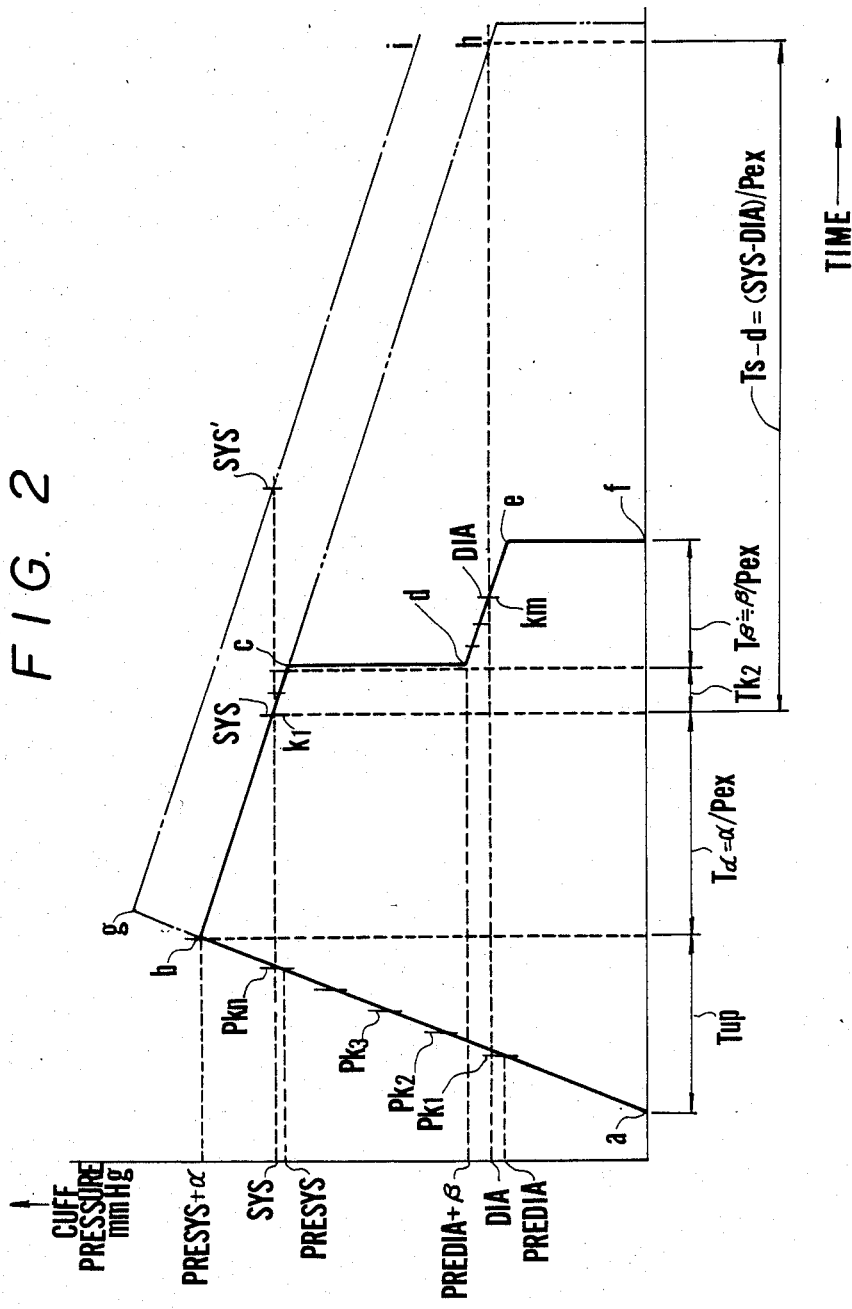
FIG. 2 is a view showing cuff pressure plotted against time and illustrating a typical process for measuring blood pressure executed by the apparatus embodied in FIG. 1.

FIGS. 2 through 5 are views useful in describing the operating principle of the apparatus embodied in FIG. 1. FIG. 2 is a view illustrating a typical process for measuring blood pressure and shows that cuff pressure begins to rise from point a to point b rapidly and without pulsation when the supply valve 11 is opened. The CPU 6 monitors the K-sounds in this interval and treats cuff pressure at the instant the first K-sound $Pk_1$ appears as the patient's predicted diastolic blood pressure, denoted PREDIA. With the rise in cuff pressure, K-sounds $Pk_2$, $Pk_3$... are detected at a generally constant period. On the basis of this period, the CPU 6 derives a maximum time interval t at which the next K-sound should appear and verifies a K-sound, if any, that appears in this interval. When the cuff pressure eventually surpasses the patient's systolic blood pressure, the K-sounds vanish and the CPU 6 treats cuff pressure that prevails at the instant the final K-sound $Pk_n$ appears as the patient's predicted systolic blood pressure, designated PRESYS. The CPU 6 then waits the prescribed time period t and closes the supply valve 11 if a K-sound is not produced within period t. The cuff pressure which prevails at this instant is an optimum pressurization cut-off point b (PRESYS+$\alpha$) for enabling rapid measurement of systolic blood pressure. According to the illustrated embodiment, a liquified gas tank is used as the pressure source 9 and the rise in cuff pressure is therefore completely free of a pulsating component. This allows even a very weak K-sound to be accurately detected as there is no risk of artifact noise appearing in the microphone in this interval of time. Thus, the appearance and disappearance of K-sounds during the rise in cuff pressure is monitored and criteria for the patient's systolic and diastolic pressures are given on the basis of the monitored K-sounds to furnish a very efficient process for measurement during depressurization of the cuff, described below.

When the constant-rate release valve 12 is opened, the cuff pressure decreases from point b to point c at a constant, regulated rate (e.g., 2–3 mmHg/sec). The appearance and disappearance of K-sounds in this interval is monitored by the CPU 6 through a method which is stricter than that set forth above. Specifically, a true K-sound signal is isolated from artifact noise by computing a logical product with the signal m synchronized to the patient's pulse, that is, by taking the AND between apparent K-sounds and the pulses constituting the signal m, and cuff pressure prevailing at the instant the first true K-sound signal appears is treated as the patient's systolic blood pressure. It should be noted that in order to verify attainment of true systolic blood pressure, the arrangement is such that the CPU 6 performs the detection of the K-sounds for a minimum of at least three heartbeats before passing judgment on the systolic blood pressure.

When systolic blood pressure has been determined, the rapid-rate pressure release valve 13 is opened to rapidly dump cuff pressure from the point c to a point d (predicted diastolic blood pressure PREDIA+$\beta$) serving as a rapid-rate release target value. The rapid reduction in pressure is permissible because detection of K-sounds in the interval from c to d is unnecessary for practical purposes. At the same time cuff pressure is dumped in this rapid fashion, the CPU 6 monitors the signal p indicative of detected cuff pressure and closes the rapid-rate release valve 13 when detected cuff pressur reaches the point d.

Thus, from the point d, the decrease in cuff pressure is again under the control of the constant-rate release valve 12 so that strict K-sound detection in accordance with the above-described method becomes possible. If at least one K-sound is detected from the rapid-rate release target value d onward, then the CPU 6 confirms that the pressure at the point d is greater than the patient's diastolic blood pressure. When the cuff pressure eventually drops belows the patient's diastolic blood pressure, the K-sounds vanish. To verify this, the CPU 6 checks that there is no K-sound for at least two beats of the signal m synchronized to the patient's pulse. The CPU 6 decides that the cuff pressure that prevails at the final occurrence of the K-sound $k_m$ is the patient's diastolic blood pressure, denoted DIA. The rapid-rate release valve 13 is opened as soon as diastolic blood pressure is determined, so that cuff pressure declines rapidly from a pont e to a point f to end one measurement cycle.

Let us now compare the above-described measurement process of the illustrated embodiment with the prior-art process in which monitoring is performed continuously from the appearance to the disappearance of the K-sounds. The prior-art process is indicated by the one-dot chain lne in FIG. 2. In the prior art, the common practice is to pressurize the cuff to a point g decided to lie within a range of 150 to 200 mmHg, followed by releasing pressure at a constant, regulated rate. By contrast, according to the illustrated embodiment, the point b is automatically detected earlier than occurrence of the patient's systolic blood pressure SYS, followed by constant venting of cuff pressure starting at the point b. In other words, the illustrated embodiment adopts a method whereby an optimum pressurization cut-off point, namely the point b, is decided automatically. This has the advantage of hastening the measurement of systolic blood pressure. Further, in the prior art, K-sounds are measured continuously during regulated pressure release from the point g, at which pressurization ends, to a point i. On the other hand, in the illustrated embodiment, cuff pressure is dumped down to the point d as soon as the point c is reached during constant-rate release of pressure, with the point c being that at which systolic blood pressure is confirmed to have been attained. This makes it possible to skip a long period of continuous measurement. Then, when diastolic blood pressure is determined during constant-rate pressure release from the point d to the point e, the measurement cycle is ended.

Let us assume a case where the pressurization point is b for both the prior-art arrangement and that of the illustrated embodiment so that we may investigate a time difference $\Delta t$ between one measurement cycle performed in accordance with the prior-art method and one measurement cycle conducting according to the method of the illustrated embodiment. The prior-art measurement cycle is indicated by the two-dot chain line in FIG. 2. Let us assume that the rate of constant cuff pressure release is $P_{ex}$ mmHg/sec in both cases. Since the patient's systolic and diastolic blood pressures are independent of the method of measurement, the aforementioned time difference $\Delta t$ may be expressed as follows:

$$\Delta t = (SYS - DIA)/P_{ex} - (Tk_2 + \beta/P_{ex})$$

It will thus be understood that a measurement in accordance with the illustrated embodiment is performed much quicker than in the prior art.

Figure 3:
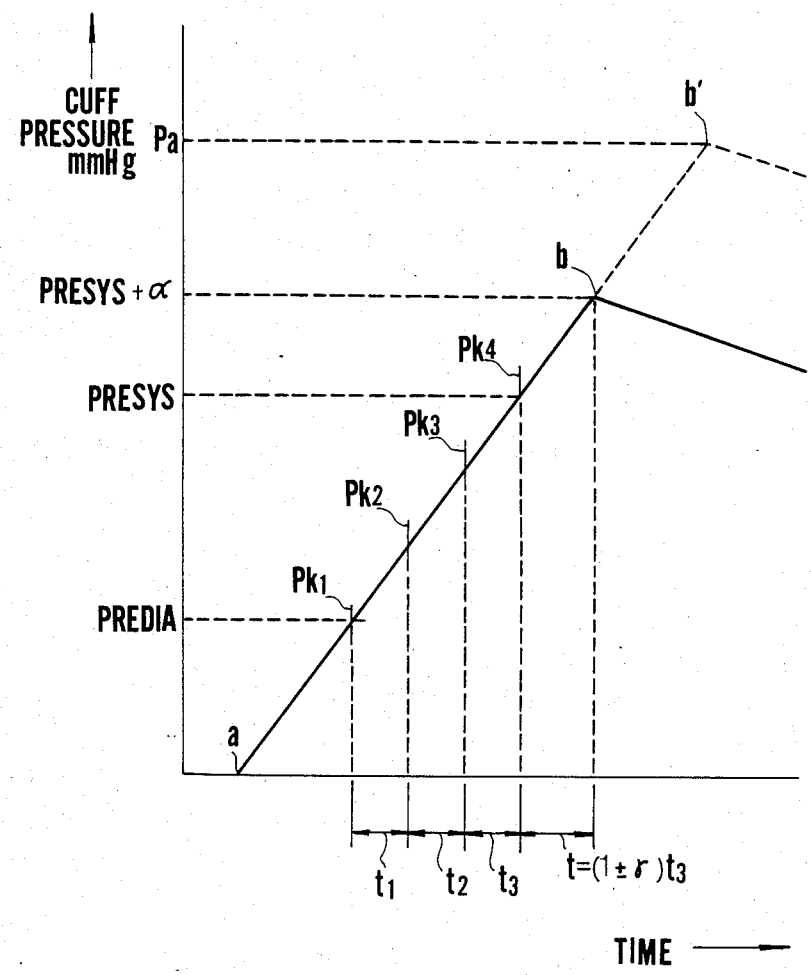
FIGS. 3(a) and (b) are more detailed views of cuff pressure plotted against time and illustrate determination of an ideal cuff pressurization point b according to the embodiment of FIG. 1.
Figure 3:
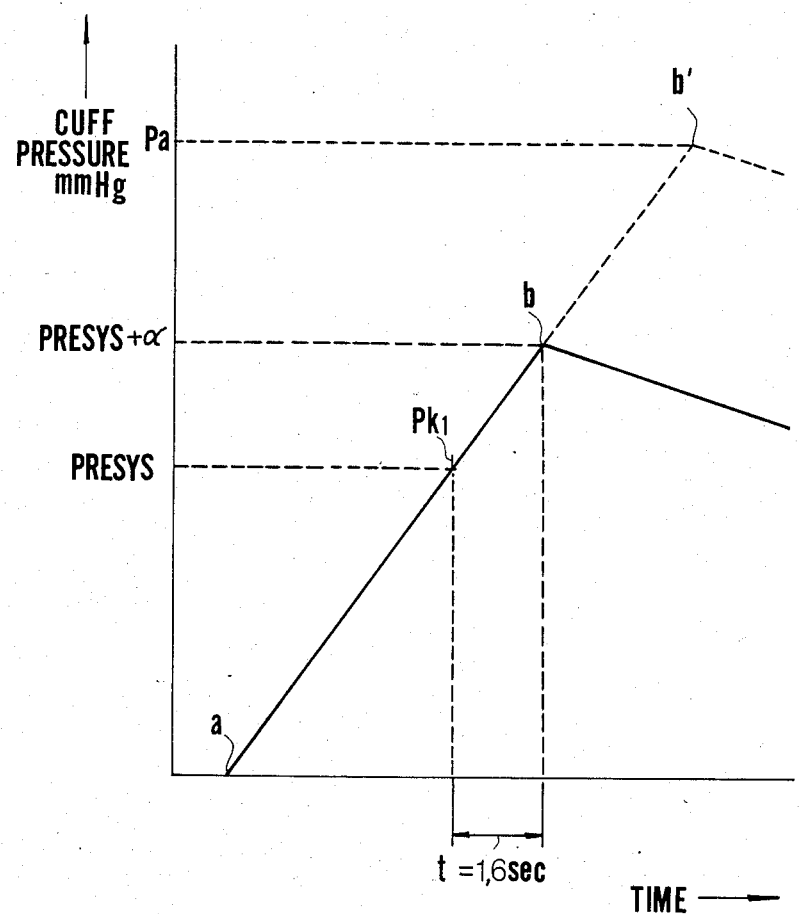

FIGS. 3(a) and (b) are views illustrating in greater detail the determination of the optimum pressurization point b according to the illustrated embodiment. In (a) of FIG. 3, the first K-sound $Pk_1$ is detected as cuff pressure is raised, and the cuff pressure that prevails at this instant is treated as the patient's predicted diastolic blood pressure PREDIA, as set forth above. When the second K-sound $Pk_2$ is detected, it is possible to predict an upper limit of a K-sound generation period from this instant. More specifically, on the basis of an initial period $t_1$ between the first and second K-sounds $Pk_1$, $Pk_2$, the CPU 6 is capable of predicting that the next K-sound $Pk_3$ will be generated within a period of time $t = (1 \pm \gamma)t_1$ at the latest, where $\gamma$ is a numerical value, decided on the basis of clinical experience, that takes into account a fluctuation in heartbeat determined by sampling and comparing data from a number of patients, In the illustrated embodiment, $\gamma$ is selected to be a fixed value of from 0.1 to 0.5. However, it is permissible to adopt values of $\gamma$ that vary in stepwise fashion in dependence upon the scale up to $t_n$, in which case a table is prepared giving values of $\pm 0.1$ to $\pm 0.5$ as $\gamma$. Long experience shows that even if a patient's K-sound generation period should happen to fluctuate widely in a short time, a value of $\gamma$ suitably selected will permit ample coverage. When the K-sound $Pk_3$ is actually produced, the CPU 6 is capable of predicting that the next K-sound $Pk_4$ will be generated within a period of time $t = (1 \pm \gamma)t_2$ at the latest, based on a new period $t_2$ between the second and third K-sounds $Pk_2$, $Pk_3$. It is of course possible to take the average of the time periods $t_1$, $t_2$ and use it in predicting the occurrence of the K-sound $Pk_4$. When a K-sound fails to occur within the next period $t = (1 \pm \gamma)t_3$, the supply valve 11 is closed immediately and the prevailing cuff pressure is deemed to be the optimum pressurization point b. This is because the cuff pressure PRESYS corresponding to the K-sound $Pk_4$ is predicted to be the systolic blood pressure of the patient.

FIG. 3(b) illustrates a situation where only one K-sound is detected during cuff pressurization. In this case, the cuff pressure that prevails at the instant the initial K-sound is detected is not treated as the patient's predicted diastolic blood pressure PREDIA. The reason is that the K-sound is considered to have escaped detection owing to its relative weakness in the vicinity of diastolic blood pressure. Since PREDIA is not decided here, a pressure difference, which is for the purpose of obtaining a rapid-rate release target value subsequent to determination of systolic blood pressure, is taken as a predetermined value (e.g. 40 mmHg). The reason for this is that pulse pressure amplitude has an average value of 40 mmHg, as confirmed by many years of clinical experience. Since the aforementioned time period t cannot be obtained in this case, the optimum pressurization point b is set by using a predetermined value (e.g., 1.6 sec) in place of the actual period $t_1$. The predetermined value of 1.6 sec is presumed to be the maximum period for a pulse rate of 38 beats per minute.

As a safety measure for a case where even a single K-sound goes undetected, a predetermined cuff pressure $P_a$ (e.g., 150-200 mmHg) at a point b' is treated as an upper limit value, as shown in (a) and (b) of FIG. 3. The CPU 6 is capable of readily executing such control by reading the cuff pressure detection signal p at an appropriate time.

Figure 4:
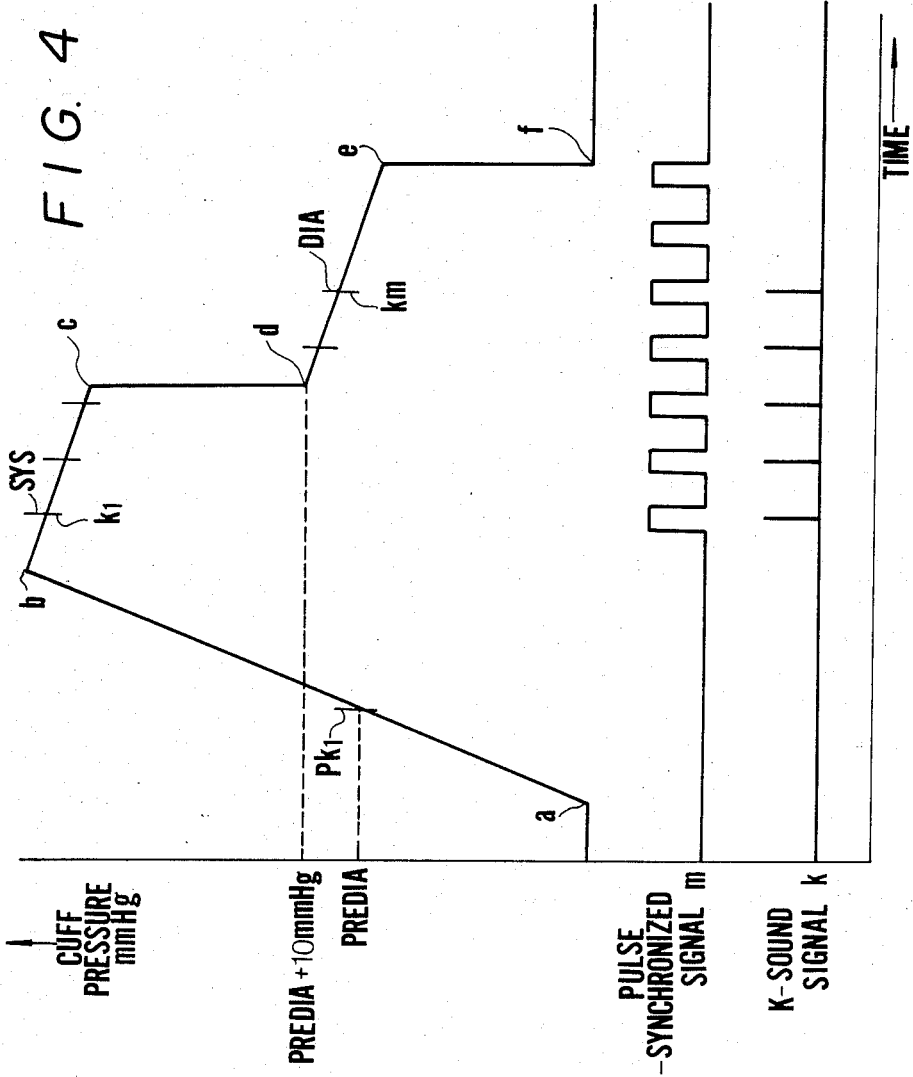
FIG. 4 is a timing chart illustrating an instance where measurement of a patient's blood pressure is performed in normal fashion by a single trial.

FIG. 4 is a timing chart illustrating an instance where measurement of a patient's blood pressure is performed in normal fashion by a single trial. A major portion of what is shown in FIG. 4 has already been described in connection with FIG. 2. FIG. 4 additionally depicts the relation between the K-sound signal k and the signal m synchronized to the patient's heartbeat. As set forth above, the signal m indicates the throbbing motion of the blood vessel occluded by the cuff and generally appears earlier than the K-sounds and vanishes later than the K-sounds. According to the illustrated embodiment, this fact is used for the purpose of eliminating artifact noise from the K-sounds by recognizing as a genuine K-sound signal only a K-sound correlated with a pulse in the signal m during regulated venting of pressure from the cuff. It should be noted that this method can also be used in K-sound detection at cuff pressurization, though this approach is not the one taken in the illustrated embodiment.

Figure 5:
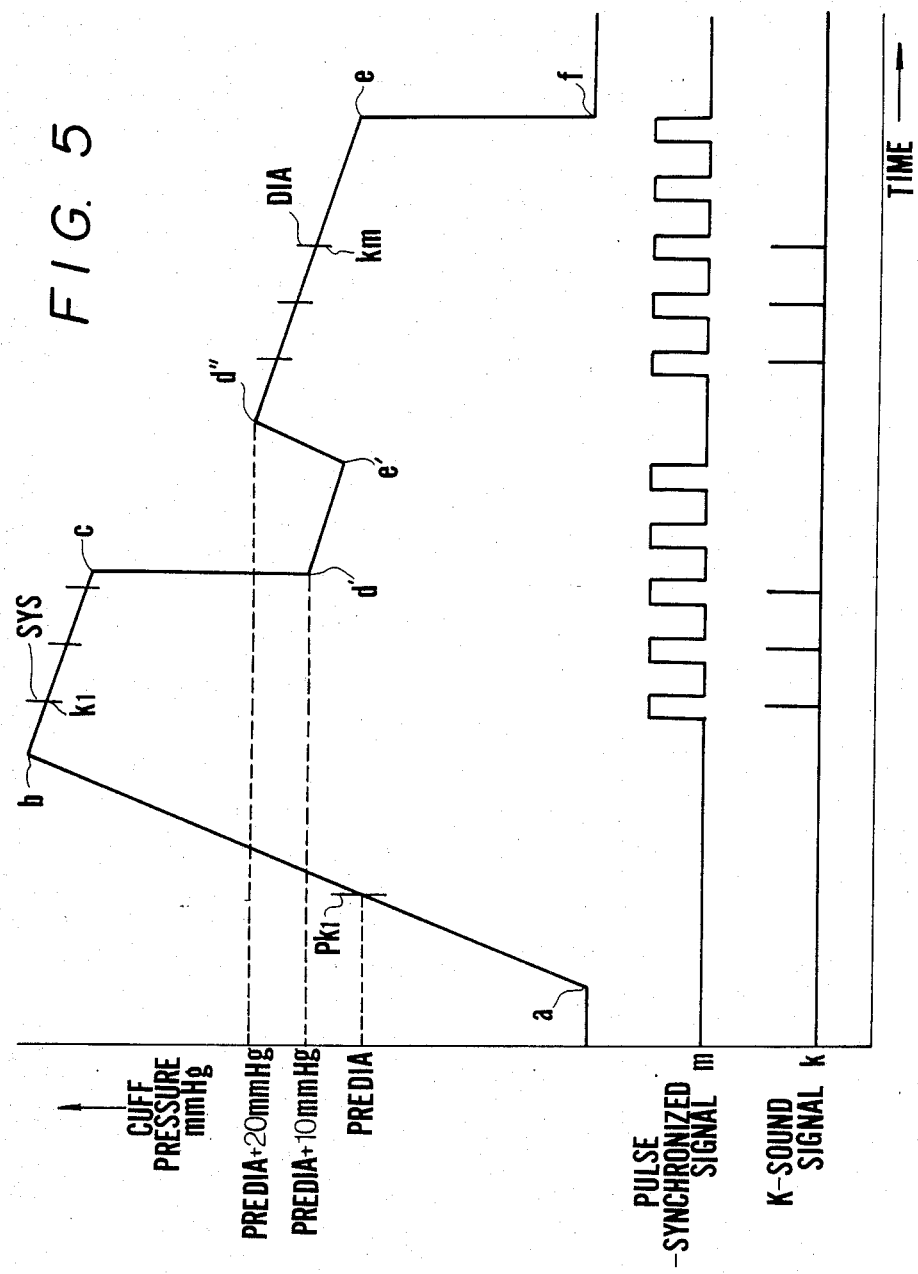
FIG. 5 is a timing chart illustrating an instance where measurement of a patient's blood pressure is performed by a single automatic retrial.

FIG. 5 is a timing chart illustrating an instance where measurement of a patient's blood pressure is performed by a single automatic retrial. In FIG. 5, the process from cuff pressurization to attainment of the point c at which systolic blood pressure SYS is determined during the course of regulated pressure release from the point b is the same as that shown in FIG. 2. FIG. 5 shows a case where predicted diastolic blood pressure PREDIA is so much lower than actual diastolic blood pressure DIA that cuff pressure has already fallen below the diastolic blood pressure DIA at attainment of a rapid-rate release target value d' (e.g., PREDIA+10 mmHg) due to rapid pressure release starting from point c. If the amount of blood pressure fluctuation (the standard deviation SD of DIA) within the measurement time period from PREDIA to DIA is taken as a reference, the constant $\beta$ (selected to be 10 mmHg in the illustrated embodiment) used in setting the rapid-rate release target value is selected to be 6 mmHg for covering 2SD and 10 mmHg for converting 3SD, by way of example. In the case of FIG. 5, the CPU 6 will count two beats of the signal m in the constant-rate pressure release interval from point d' to point e', but it will not detect a K-sound in this interval. Accordingly, approximately 20 mmHg of pressure is applied to the cuff pressure prevailing at the point e' to elevate cuff pressure to a point d". FIG. 5 shows that the cuff pressure at this time attains a value equivalent to approximately PREDIA+20 mmHg, as verified by experience. Therefore, if a retrial of this kind is performed three times, cuff pressure will rise to a value of PREDIA+40 mmHg as a result, thereby enabling the diastolic blood pressure DIA to be fully covered. It has been set forth above that pulse pressure amplitude has an average value of about 40 mmHg. When the cuff pressure rises to the point d", there is again a transition to constant-rate release of pressure from the cuff. In FIG. 5, the cuff pressure now covers the diastolic blood pressure DIA, so that several K-sounds are detected during the pulses constituting the signal m synchronized to the patient's pulse. When cuff pressure eventually falls below the patient's diastolic blood pressure DIA, the K-sounds vanish. To verify this, the CPU 6 checks that there is no K-sound for at least two beats of the signal m. The CPU 6 decides that the cuff pressure prevailing at the final occurrence of the K-sound $k_m$ is the patient's diastolic blood pressure DIA. The rapid-rate release valve 13 is opened as soon as diastolic blood pressure is determined, so that cuff pressure declines rapidly from point e to point f to end the measurement process.

Figure 6:
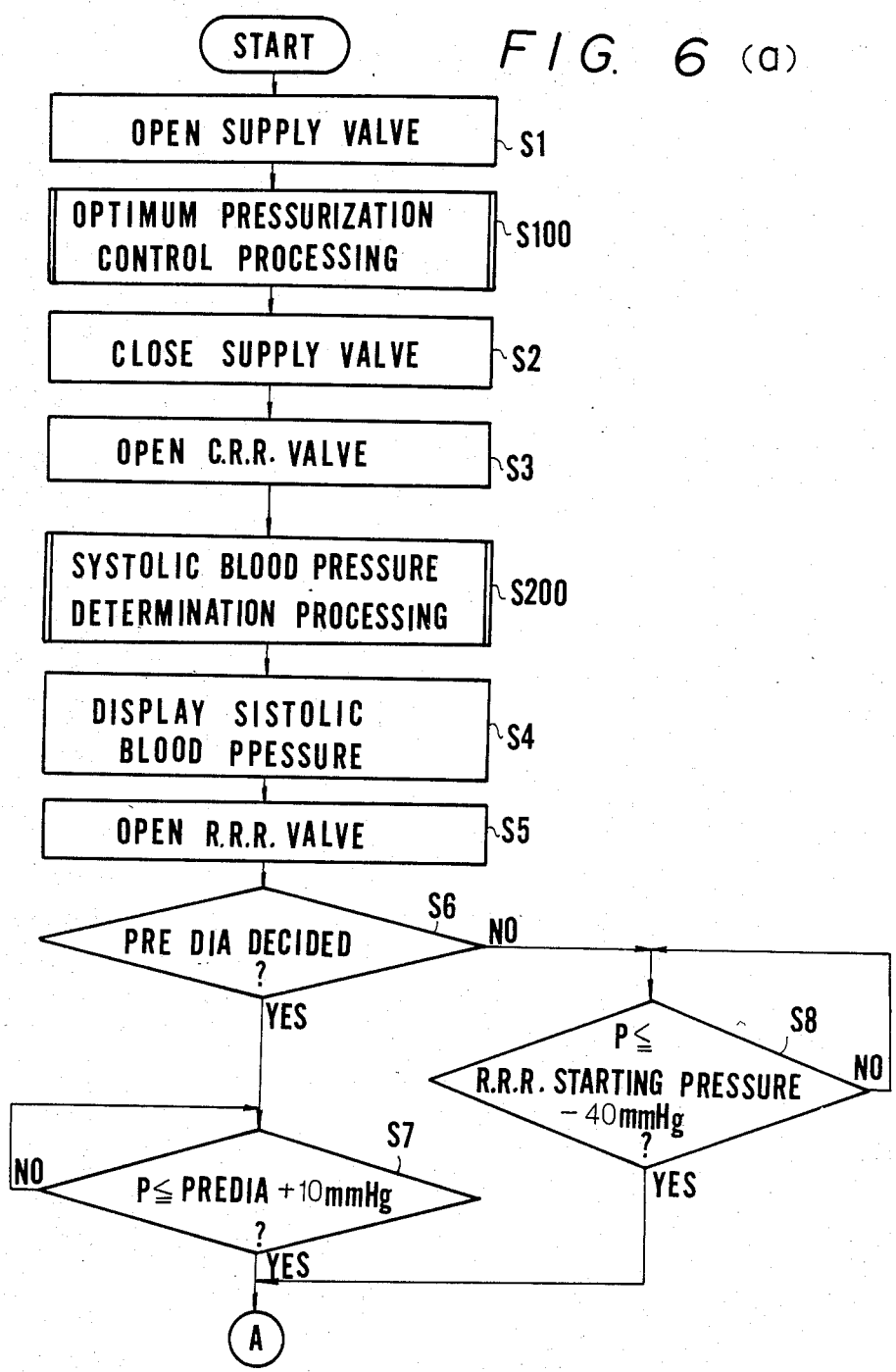
FIGS. 6(a), 6(b), and 6(c) are a flowchart illustrating the control sequence of a blood pressure measuring process performed by control means included in the apparatus of FIG. 1.
Figure 6:
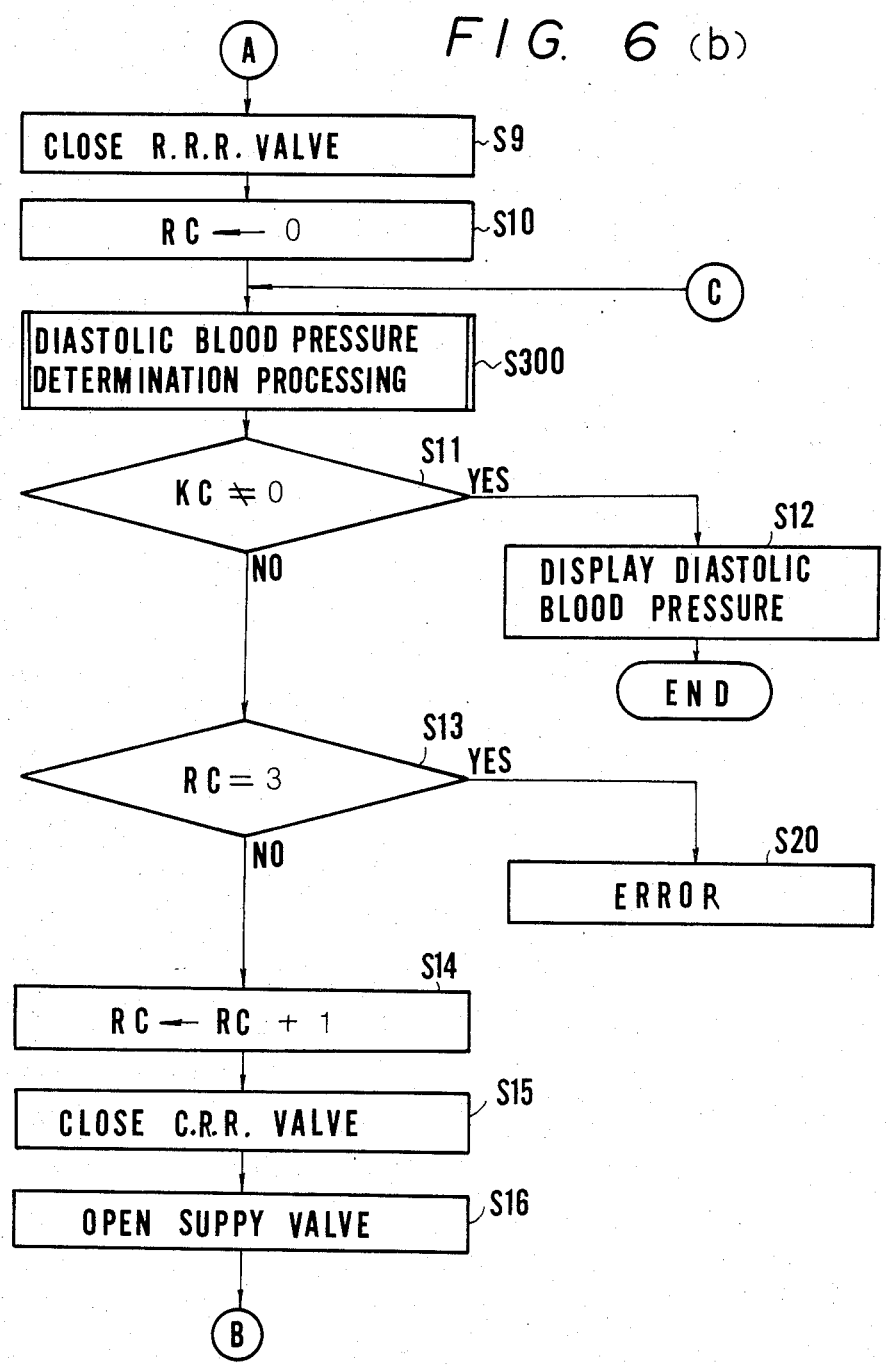

FIGS. 6 through 9 show program control sequences associated with the apparatus of the illustrated embodiment for executing control in accordance with the operating principle described above. FIG. 6 is a flowchart illustrating the control sequence of the blood pressure measuring process performed by the control means 19 in FIG. 1. At a step S1 of the flowchart, the supply valve 11 is opened, so that an optimum pressurization control process may be executed at a step S100. Though the optimum pressurization control process will be described in detail below, this is a process for deciding the optimum pressurization cut-off point b of the cuff. Following execution of step S100, the supply valve 11 is closed at a step S2 and the constant-rate release valve 12 is opened at a step S3. During regulated pressure release following pressurization, a systolic blood pressure determination process is executed at a step S200, followed by display of systolic blood pressure at a step S4. As soon as systolic blood pressure is determined, the rapid-rate pressure release valve 13 is opened to dump cuff pressure at a rapid rate. Next, at a step S6, it is determined whether the predicted diastolic blood pressure PREDIA has been decided in the optimum pressurization control process. If the decision at the step S6 is affirmative (YES), then the CPU 6 waits for the cuff pressure to fall to the rapid-rate release target value (PREDIA+10 mmHG) at a step S7. If the decision at the step S6 is negative (NO), then the program moves to a step S8 and the CPU 6 waits for depressurization down to an alternative rapid-rate release target value (rapid-rate release starting pressure minus 40 mmHg). When the target value is reached, the rapid-rate release valve 13 is closed at a step S9 so that a transition can be made to regulated pressure release with the valve 13 closed. It is of course possible to exercise control in such a manner that the constant-rate release valve 12 is closed in advance during the rapid-rate pressure release described above. A retry counter RC is initialized to a value of zero at a step S10. The retry counter RC is adapted to count the number of retrial measurement cycles in a case where diastolic blood pressure cannot be measured successfully by a single attempt. A diastolic blood pressure determination process is executed at a step S300 during constant-rate release of pressure, which takes place after rapid-rate release. The condition for returning from the step S300 is non-detection of a K-sound for two beats of the signal m synchronized to the patient's pulse. The value of the count recorded by a K-sound counter KC is checked at a step S11. If the value of the count is non-zero, this indicates that one or more K-sounds have been detected and the program moves to a step S12 to display the diastolic blood pressure. This ends the measurement process.

If the decision at the step S11 is that the KC is zero, this indicates that a retrial is required and the program moves to a step S13, where it is checked whether a retrial has been performed three times. If it has, then the program moves to a step S20, where an error process is executed. If a retrial has not been performed three times at the step S13, the program moves to a step S14 to increment the status of the retry counter RC by +1. The constant-rate release valve 12 is then closed at a step S15 and the supply valve 11 opened at a step S16. This is followed by a step S17, at which the CPU 6 waits for the cuff pressure to attain a value equivalent to the pressurization starting pressure plus 20 mmHg. The supply valve 11 is closed and the constant-rate release valve 12 opened at steps S18, S19, respectively, and the program returns to the step S300 to execute the diastolic blood pressure determination process.

Figure 7A:
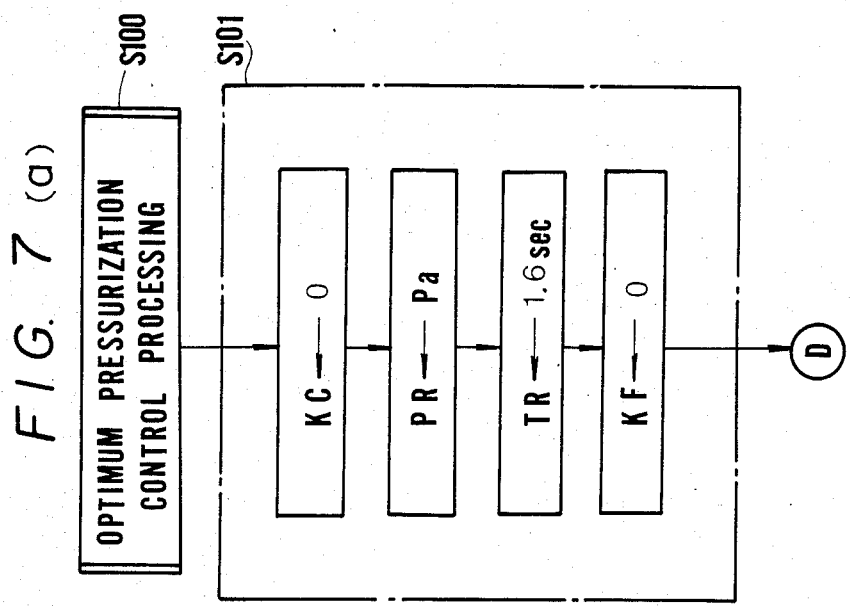
Figure 6C:
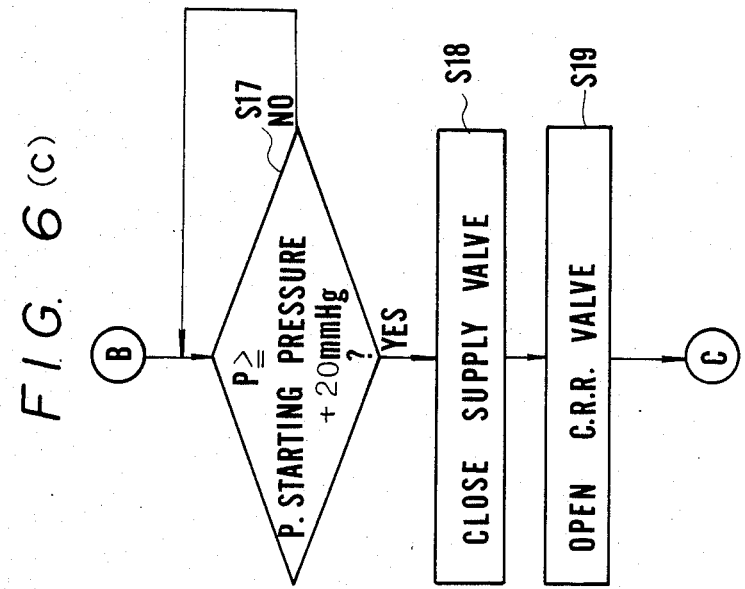
Figure 7B:
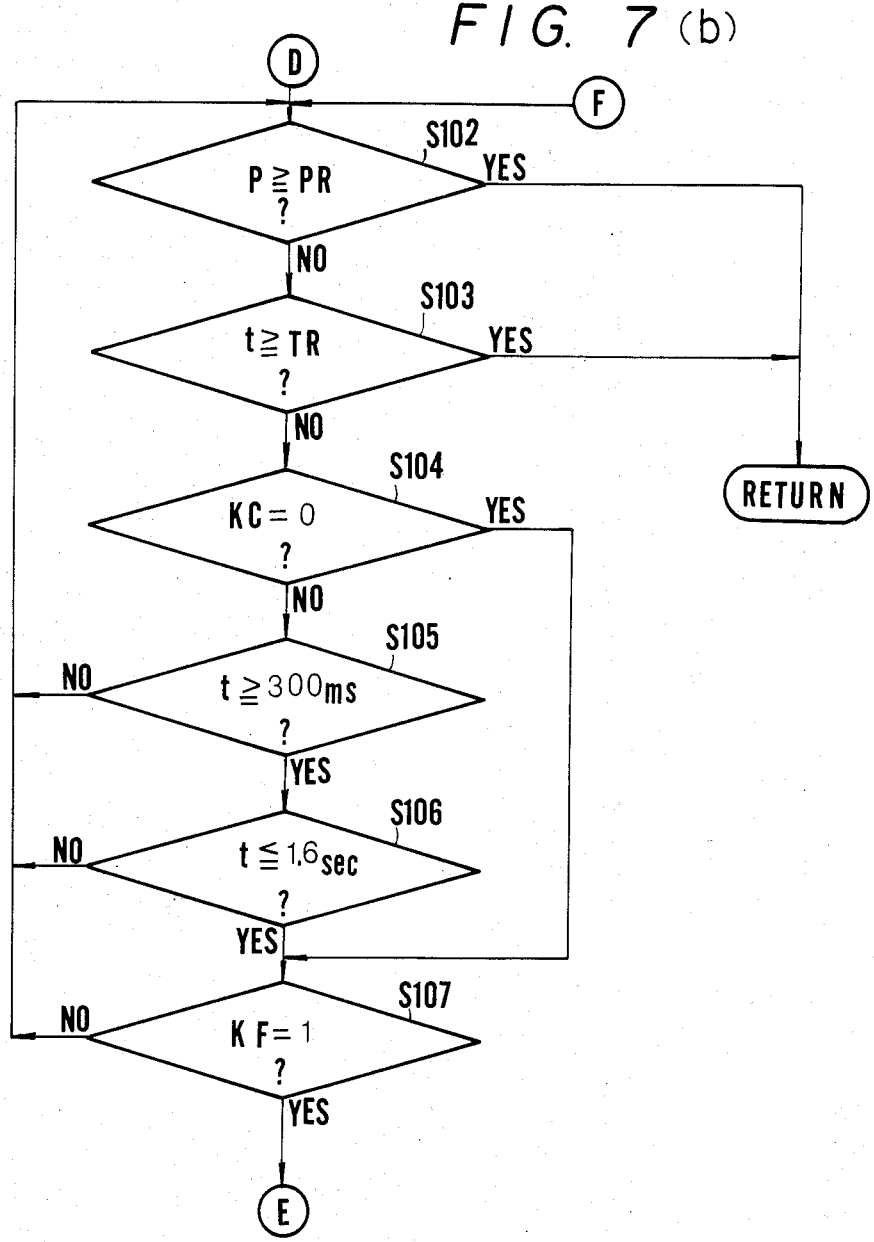

FIG. 7 is a flowchart illustrating the optimum pressurization control process. A series of initialization processes is performed at a step S101. Specifically, the K-sound counter KC is initialized to zero, a pressure register PR to the upper limit value Pa of cuff pressure, a timer register TR to the constant of value 1.6 sec, and a K-sound detection flag to logical "0". The K-sound detection flag KF goes to logical "1" in response to a leading edge of the K-sound signal k. Upon sensing this "1" logic, the CPU 6 resets the flag. Next, it is determined at a step S102 whether the cuff pressure detection signal p has attained the pressurization limit PR (in this case, the upper limit value Pa). If this value has not been attained, it is determined at a step S103 whether the time TR set in a timer t has expired. The timer, which is for the purpose of detecting whether a preceding K-sound is followed by another K-sound within a predetermined period of time, is initially not in the operative state. Since the decision at the step S103 will therefore be NO, the program moves to a step S104, where the state of the K-sound counter KC is investigated. The status of the counter KC will be zero until the first K-sound $Pk_1$ is found. Processing therefore jumps to a step S107 to investigate the status of the K-sound detection flag KF. If KF is not logical "1", then the program returns to the step S102. This loop is repeated until the first K-sound occurs. When the decision at the step 107 is that a K-sound has been detected, a step S108 is executed, at which the value of the prevailing cuff pressure detection signal p is stored in a predicted blood pressure memory (PRE-memory) so that this value may later be used as the predicted diastolic blood pressure PREDIA. Next, at a step S109, KC is incremented by +1, followed by determining at a step S110 whether KC is 2 or more. If KC is less than 2, then the upper limit t of the period at which the next K-sound will be generated cannot be calculated. The program moves to a step S112 as a result to set the timer into operation.

Next, it is again determined at the step S102 whether the pressurization limit has been attained. If it has not, it is determined at the step S103 whether the time TR set in the timer has expired. At this moment, the status of the register TR will be the constant 1.6 sec, and the decision at the step S103 will be YES if the next K-sound has not occurred within 1.6 sec. The process therefore returns to the step S2 of FIG. 6 and the optimum pressurization point b is decided for the case where only one K-sound is detected during the course of cuff pressurization. If the decision at the step S103 is that the time has not yet expired, the step S104 is executed to investigate KC. If at least one K-sound has occurred, then a step S105 is always executed to isolate a K-sound from artifact noise. More specifically, it is determined at the step S105 whether the status of the timer is 300 mS or more. By utilizing the fact, learned from experience, that a K-sound will not be followed by another K-sound within 300 mS (which would be equivalent to a heartbeat rate of more than 200 beats per minute), the earlier K-sound signal is ignored. Then it is determined at a step S106 whether the status of the timer t is greater than 1.6 sec. By utilizing the fact, learned from experience, that a K-sound will not be followed by another K-sound more than 1.6 sec later (which would be equivalent to a heartbeat rate of less than 38 beats per minute), the latter K-sound signal is ignored. Therefore, K-sounds only within the limits satisfying both the steps S105, S106 are investigated. When a K-sound is detected at the step S107, the cuff pressure p prevailing at this time is stored in memory at the step S108, KC is incremented by +1 at the step S109, and KC is checked at the step S110. If KC is equal to or greater than 2, then the upper limit of the period at which a K-sound should be generated next can be calculated. The program then moves to a step S111, where the timer register TR is set to $(1 \pm \gamma)$. Though the status of the register TR has until now been the constant 1.6 sec, from this moment onward use is made of a value obtained by multiplying the immediately preceding period t by $(1 \pm \gamma)$. This enables execution of optimum pressurization control for a more rapid and accurate measurement conforming to the condition of the patient. The timer is restarted at the step S112, followed by a return to the step S102. When the K-sounds eventually vanish, expiration of time is detected at the step S103 and processing exits to decide the optimum pressurization point b for the case where two or more K-sounds are detected during the course of cuff pressurization.

Figure 8:
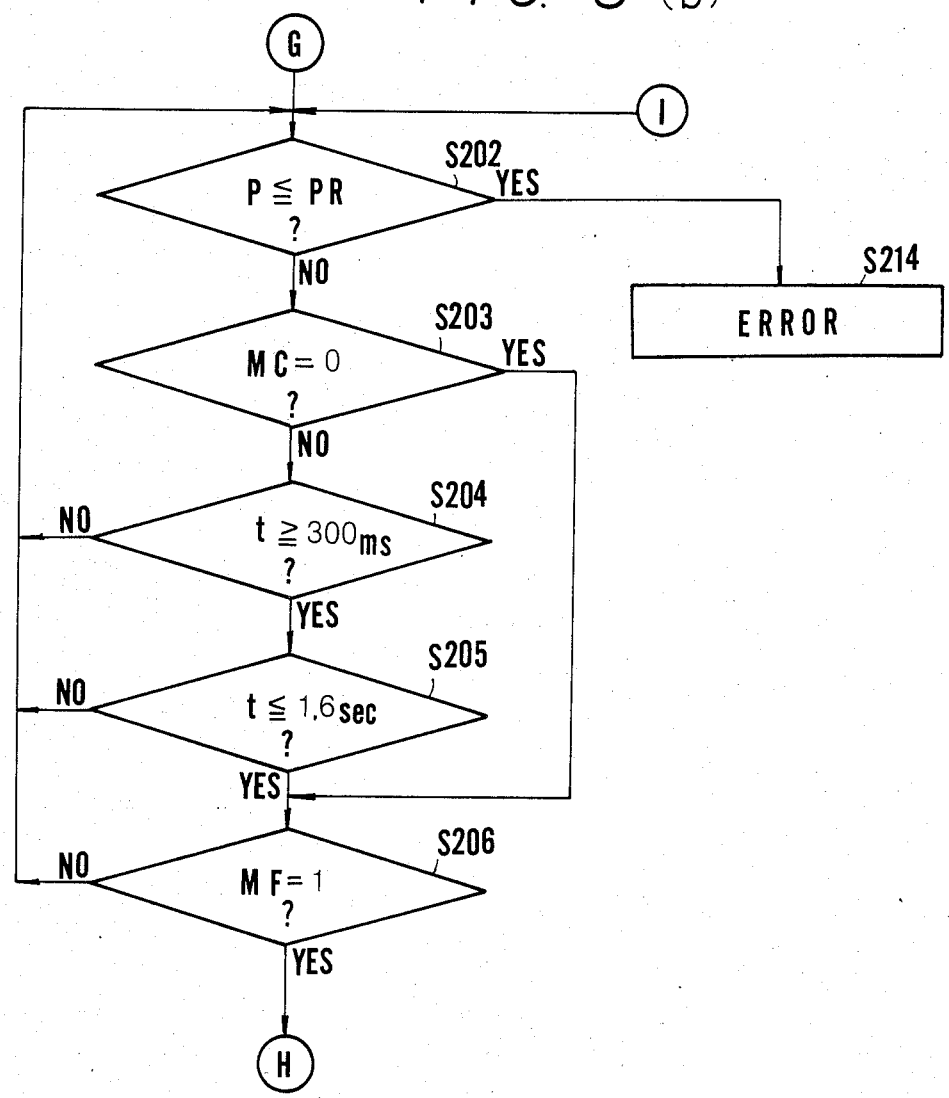
FIGS. 8(a), 8(b), and 8(c) are a flowchart illustrating a processing sequence performed by blood pressure determining means included in the apparatus of FIG. 1 for determining systolic blood pressure.
Figure 8:
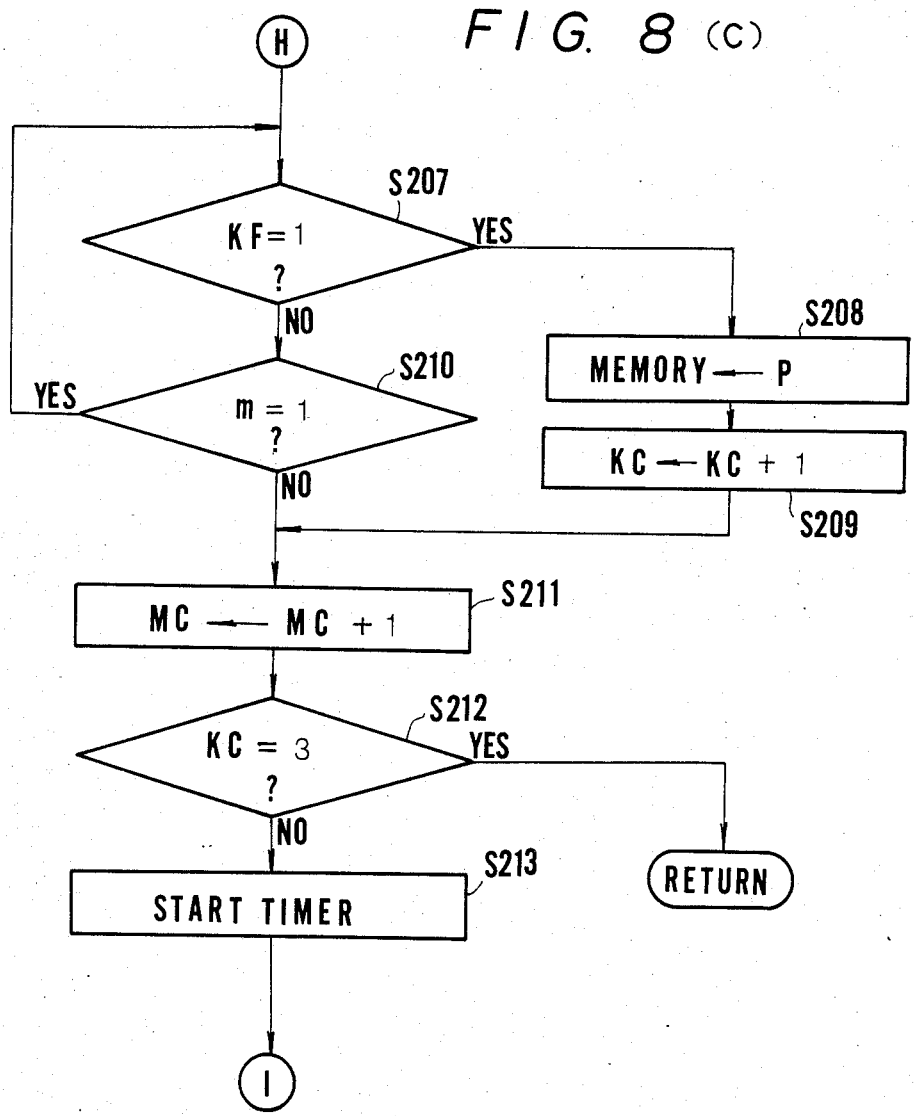

FIG. 8 is a flowchart illustrating the systolic blood pressure determination process. A series of initialization processes is performed at a step S201. Specifically, a counter MC for the patient's pulse is initialized to zero, the K-sound counter to zero, the pressure register PR to a lower limit value Pb of depressurization, a patient pulse detection flag MF to logical "0", and the K-sound detection flag KF to logical "0". The lower limit value Pb may be a value below which a systolic blood pressure cannot possibly exist. The pulse detection flag MF goes to logical "1" when a leading edge of the signal m is sensed. When the "1" logic is sensed the CPU 6, the flag is reset. When a depressurization limit is exceeded at a step S202, the program moves to a step S214 for error processing. In practice, however, this condition almost never occurs. The status of the patient pulse counter MC is checked at a step S203. With the exception of the fact that steps S204, S205, S206 deal with the signal m sychronized to the patient's pulse, these steps are similar to the above-described steps S104, S105, S106 of FIG. 7. The status of the pulse detection flag MF is checked at a step S206. The foregoing loop is repeated until the first MF is found. When this occurs, i.e., when MF=logical "1", the status of the K-sound flag KF is investigated at a step S207. When KF is detected, i.e., when KF=logical "1", the prevailing cuff pressure p is stored in memory at a step S208 and KC is incremented by +1 at a step S209. When no K-sound is detected, i.e., when the answer at the step S207 is NO, processing advances to a step S210, where the level of the signal m is investigated. K-sound detection is repeated while the signal level is at logical "1". This is to eliminate artifact noise by detecting only those K-sounds that occur during these high logic level pulses of the signal m. When the level of the signal m reverts to logical "0", processing advances to a step S211 to increment the MC by +1. Next, at a step S212, KC is checked and, if K=3 holds, systolic blood pressure SYS is determined and processing returns to the step S4 in FIG. 6. If KC is less than 3 at the step S212, the timer is activated at a step S213 and processing returns to the step S202. Subsequent processing is similar to that set forth in connection with FIG. 7 and is not described here to avoid prolixity.

Figure 9:
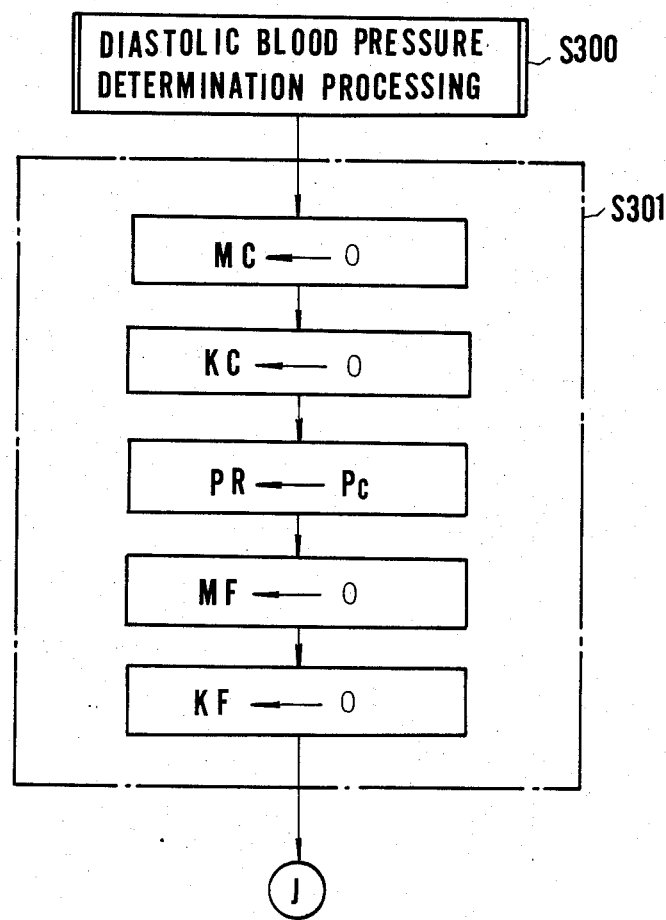
FIGS. 9(a), 9(b), and 9(c) are a flowchart illustrating a processing sequence performed by the blood pressure determining means for determining diastolic blood pressure.
Figure 9:
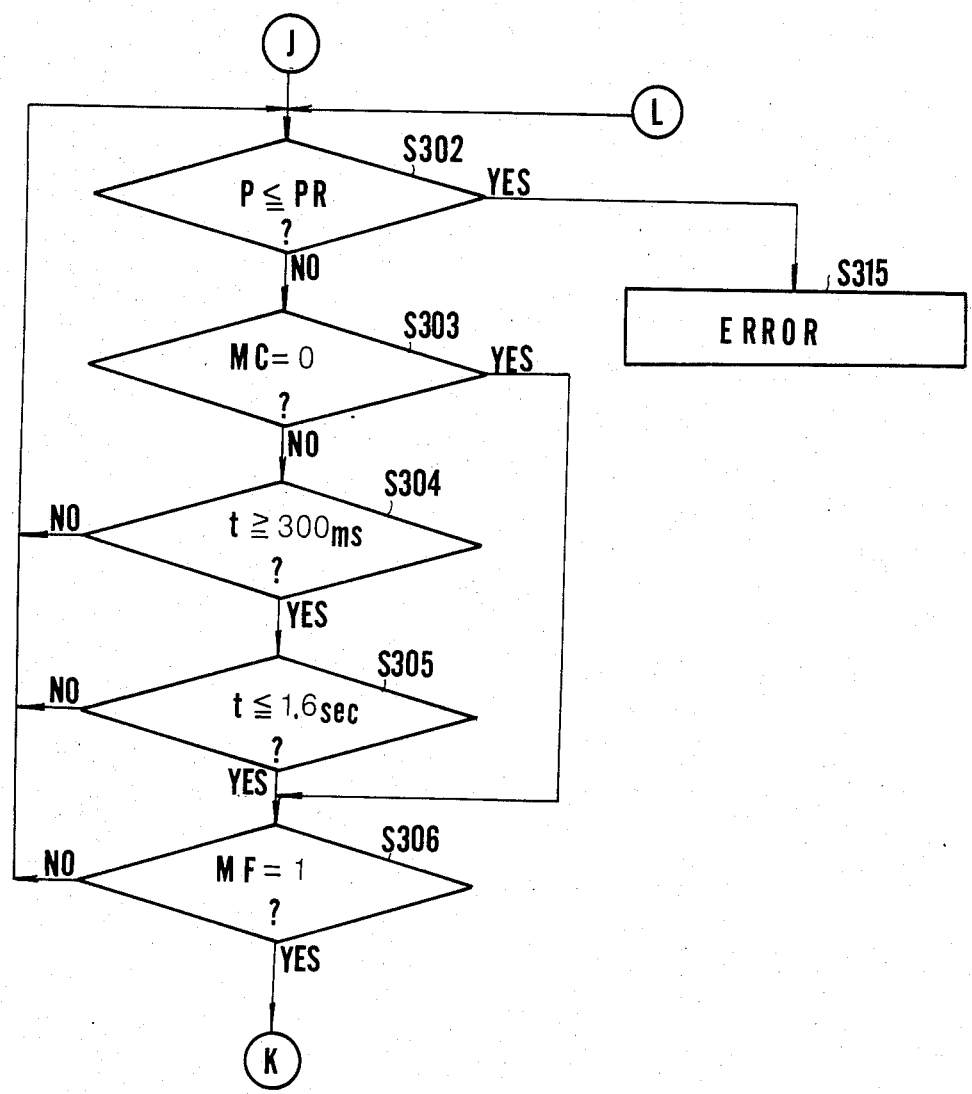
Figure 9:
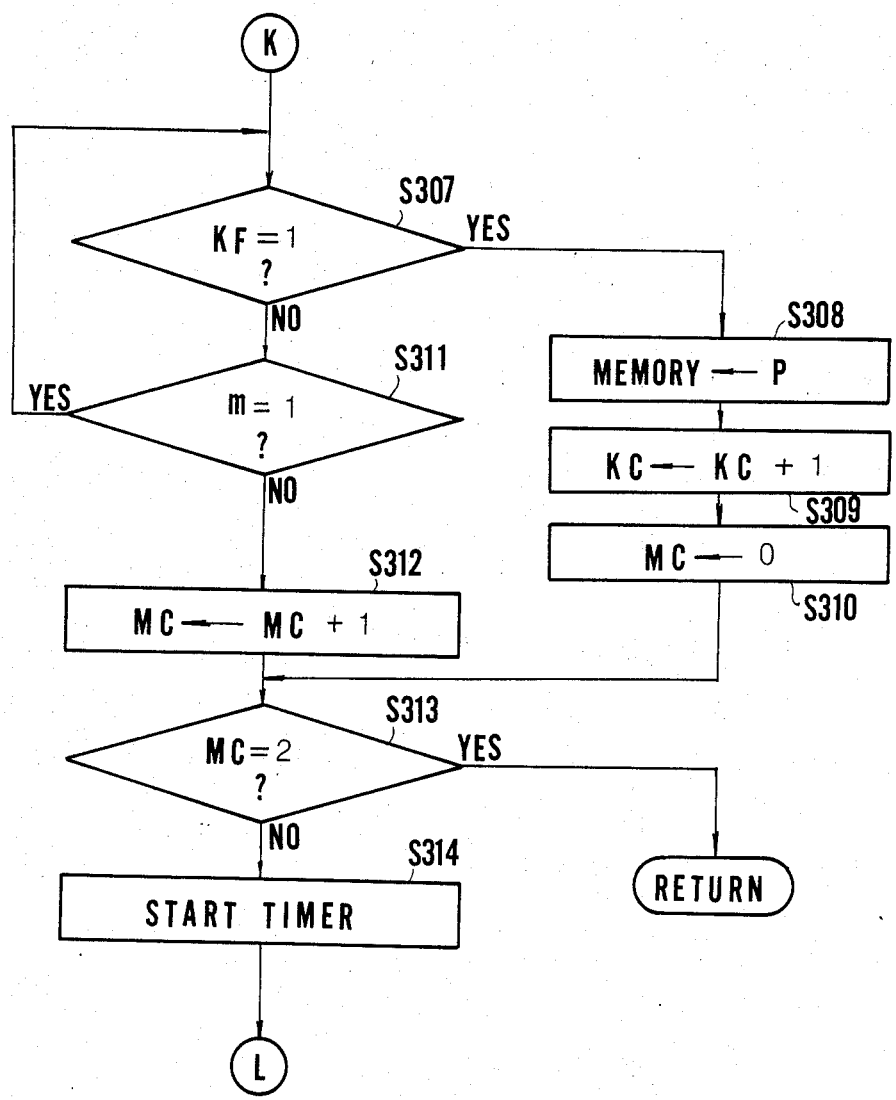

FIG. 9 is a flowchart illustrating the diastolic blood pressure determination process. A series of initialization processes is performed at a step S301, one of which is to set the pressure register PR to an even smaller lower limit value Pc of depressurization in comparison with lower limit Pb of FIG. 8. The step S301 is identical with the step S201 of FIG. 8 in other respects. Further, steps S302–S307 are similar to the steps S202–S207 of FIG. 8 and need not be described here.

When the K-sound flag KF (i.e., "1") is detected at the step S307, the cuff pressure prevailing at this instant is stored in memory at a step S308, KC is incremented by +1 at a step S309, and MC is reset at a step S310. Diastolic blood pressure is determined upon detecting MF for only two consecutive beats following detection of at least one KF. It is for this reason that MC is reset following KF detection. If the level of the signal m is detected to be logical "0" at a step S311, MC is incremented at a step S312 despite the fact that a K-sound is not detected at the step S307. When this path of the flowchart is traversed, this indicates that a K-sound has not occurred during high logic level of the signal m. It is determined at a step S313 whether MC is 2. If it is, then processing returns to the step S11 of FIG. 6. If MC is less than 2, a timer is activated at a step S314 and processing returns to the step S302. Subsequent processing is similar to that described above in conjunction with FIG. 7 or FIG. 8 and need not be described here.

The apparatus of the present invention is small in size and light in weight, and the liquified gas tank can be carried at the patient's waist as mentioned above. Accordingly, the invention is applicable not only to patients confined to bed, for the entire apparatus can be carried about by a patient without interfering with the patient's daily routine. This allows the patient to take data readings at, say, 30 minute intervals over an entire day without repairing to a special place or location. In such case, the timer means internally of the CPU and other units will be adapted to control the start of measurement periodically at predetermined times. This means that if the first measurement is performed at a time which is not on the hour or on the half-hour, i.e., at a time such as 9:15, the next and subsequent measurements for collecting data will be performed on the hour or on the half-hour, these being moments favorable, in terms of statistics, for such data collection. The reason for this is that adopting such an arrangement improves preparedness to receive a patient's measurements and facilitates the study of fluctuation patterns and of reproducibility by enabling a comparison of data, taken from a number of patients, along an identical time axis.

As many apparently widely different embodiments of the present invention can be made without departing from the spirit and scope thereof, it is to be understood that the invention is not limited to the specific embodiments thereof except as defined in the appended claims.

What we claim is:

1. An apparatus for automatically measuring blood pressure, comprising:
   a cuff adapted to be affixed to a limb of a patient;
   pressurizing means for rapidly pressurizing said cuff;
   depressurizing means for sensing cuff pressure and for producing a cuff pressure signal indicative of the cuff pressure;
   K-sound sensing means for sensing K-sounds from the limb of the patient and for producing a K-sound signal indicative of the K-sounds;
   timer means for measuring a period of each K-sound signal produced during initial pressurization of said cuff by said pressurizing means;
   holding means for holding a predicted period of the K-sound signal;
   updating means for diciding a new predicted period based on a measured period and successively updating the predicted period held in said holding means by the new predicted period;
   sensing means for generating a timing signal in response to failure of a next K-sound signal to appear within the predicted period held in said holding means; and
   control means for immediately halting the initial pressurization in response to the timing signal, and for thereafter causing said depressurizing means to start depressurization in order to measure blood pressure.

2. The apparatus according to claim 1, wherein said pressurizing means comprises a liquified gas tank as a source of pressure.

3. The apparatus according to claim 1, wherein said updating means decides a new predicted period within a range of ½ to 1½ of a preceding period.

4. A method of automatically measuring blood pressure, comprising steps of:
   rapidly pressurizing a cuff affixed to a limb of a patient;
   seting a target pressure value, indicating a pressure down to which the cuff is to be rapidly vented, on the bassis of a cuff pressure which prevails at initial appearance of a K-sound signal during pressurization of the cuff;
   halting the pressurization in response to extinction of K-sound signals during the pressurization;
   determining systolic blood pressure of the patient based on a first K-sound signal appearing during slow depressurization immediately after the pressurization is halted and existence of the cuff pressure signal when the first K-sound signal appears;
   rapidly venting the cuff down to the target pressure value after the systolic blood pressure is determined; and
   determining diastolic blood pressure of the patient based on a second K-sound signal sensed immediately prior to extinction of the K-sound signals during slow depressurization after the rapid venting of the cuff ends and existence of the cuff pressure signal when the second K-sound signal is sensed.

5. An apparatus for automatically measuring blood pressure, comprising:
   a cuff adapted to be affixed to a limb of a patient;
   pressurizing means for rapidly pressurizing said cuff;
   fast depressurizing means for depressurizing said cuff at a first rate;
   slow depressurizing means for depressurizing said cuff at a second rate slower than the first rate;
   pressure sensing means for sensing cuff pressure and for producing a cuff pressure signal indicative of the cuff pressure;
   K-sound sensing means for sensing K-sounds from the limb of the patient and for producing a K-sound signal indicative of the K-sounds;
   setting means for setting a target pressure value, indicating a pressure down to which the cuff is to be rapidly vented, on the basis of a cuff pressure signal which prevails at initial appearance of a K-sound signal during pressurization performed by said pressurizing means;
   halting means for halting the pressurization in response to extinction of the K-sound signals during the pressurization;
   systolic blood pressure determining means for determining systolic blood pressure of the patient based on a first K-sound signal appearing during depressurization performed by said slow depressurizing means immediately after the pressurization is halted and existence of the cuff pressure signal when the first K-sound signal appears;

rapid venting means for causing said fast depressurizing means to rapidly vent the cuff down to the target prssure value after the systolic blood pressure is determined; and diastolic blood pressure determining means for determining diastolic blood pressure of the patient based on a second K-sound signal sensed immediately prior to extinction of the K-sound signals during depressurization performed by said slow depressurizing means after the rapid venting of the cuff ends and existence of the cuff pressure signal when the second K-sound signal is sensed.

6. The apparatus according to claim 5, wherein said pressurizing means comprises a liquified gas tank as a source of pressure.

7. The apparatus according to claim 5, wherein said target pressure value is obtained by adding a predetermined value to the cuff pressure signal at the initial appearance of the K-sound signal during the pressurization performed by said pressurizing means.

8. An apparatus for automatically measuring blood pressure, comprising:

a cuff adapted to be affixed to a limb of a patient;

pressurizing means for rapidly pressurizing said cuff;

fast depressurizing means for depressurizing said cuff at a first rate;

slow depressurizing means for depressurizing said cuff at a second rate slower than the first rate;

pressure sensing means for sensing cuff pressure and for producing a cuff pressure signal indicative of the cuff pressure;

extracting means for extracting a pulse pressure signal from the cuff pressure signal and for outputting a pulse-synchronized signal;

K-sound sensing means for sensing K-sounds from the limb of the patient and for producing a K-sound signal indicative of the K-sounds;

setting means for setting a target pressure value, which is a pressure down to which the cuff is to be rapidly vented, on the bassis of existence of the pulse-sychronized signal to initial appearance of the K-sound signal during pressurization performed by said pressurizing means;

halting means for halting the pressurization in response to extinction of the K-cound signals during the pressurization;

systolic blood pressure determining means for determining systolic blood pressure of the patient based on a first K-sound signal appearing during depressurization performed by said slow depressurizing means immediately after the pressurization is halted and existence of the cuff pressure signal when the first K-sound signal appears;

rapid venting means for causing said fast depressurizing means to rapidly vent the cuff down to said target pressure value after the systolic blood pressure is determined;

diastolic blood pressure determining means for determining diastolic blood pressure of the patient based on a second K-sound signal sensed immediately prior to extinction of the K-cound signals during depressurization performed by said slow depressurizing means after the rapid venting of the cuff ends and existence of the cuff pressure signal when the second K-sound signal is sensed;

counting means for counting a predetermined number of the pulse-synchronized signals generated during depressurization performed by said slow depressurizing means after said rapid venting ends;

repressurization control means for causing said pressurizing means to repressurize the cuff by a predetermined amount of pressure in response to failure of a K-sound signal ot be sensed by the time said counting means counts said predetermined number of pulse-synchronized signals; and redetermination means for causing said diastolic blood pressure determining means to determine diastolic blood pressure during the depressurization performed by said slow depressurizing means immediately after the repressurization ends.

9. An apparatus for automatically measuring blood pressure, comprising:

a cuff adapted to be affixed to a limb of a patient;

pressurizing means for rapidly pressurizing said cuff at a first rate;

slow depressurizing means for depressurizing said cuff at a second rate slower than the first rate;

pressure sensing means for sensing cuff pressure and for producing a cuff pressure signal indicative of the cuff pressure;

K-sound sensing means for sensing K-sounds from the limb of the patient and for producing a K-sound signal indicative of the K-sounds;

halting means for halting the pressurization in response to extinction of the K-sound signals during the pressurization;

systolic blood pressure determining means for determining systolic blood pressure of the patient based on a first K-sound signal appearing during depressurization performed by said slow depressurizing means immediately after the pressurization is halted and existence of the cuff pressure signal when the first K-sound signal appears;

rapid venting means for causing said fast depressurizing means to rapidly vent the cuff by a predetermined amount of pressure after the systolic blood pressure is determined; and diastolic blood pressure determining means for determining diastolic blod pressure of th patient based on a second K-sound signal sensed immediately prior to extinction of the K-sound signals during depressurization performed by said slow depressurizing means after the rapid venting of the cuff ends and existence of the cuff pressure signal when end second K-sound signal is sensed.

10. The apparatus according to claim 9, wherein the predetermined amount of pressure is 40 mmHg.

* * * * *

UNITED STATES PATENT AND TRADEMARK OFFICE
CERTIFICATE OF CORRECTION

PATENT NO. : 4,660,567

DATED : April 28, 1987

INVENTOR(S) : Kaneko et al.

It is certified that error appears in the above-identified patent and that said Letters Patent is hereby corrected as shown below:

Col. 9, line 9, "pont" should be --point--.

Col. 14, line 34, "sychronized" should be --synchronized--.

Col. 16, line 20, "seting" should be --setting--;
line 22, "bassis" should be --basis--.

Col. 17, line 6, "prssure" should be --pressure--;
line 44, "bassis" should be --basis--;
line 45, "sychronized" should be --synchronized--;
line 45, "to" should be --at--.

Col. 18, line 4, "K-Cound" should be --K-sound--;
line 16, "ot" should be --to--;
line 52, "th" should be --the--.
line 52, "blod" should be -- blood --.

Signed and Sealed this

Fifth Day of January, 1988

Attest:

DONALD J. QUIGG

Attesting Officer   Commissioner of Patents and Trademarks